United States Patent [19]
Mochizuki et al.

[11] Patent Number: 5,784,153
[45] Date of Patent: Jul. 21, 1998

[54] METHOD FOR DETECTING CAUSE OF ABNORMAL PORTION PRESENT ON SURFACE OF STEEL PRODUCT

[75] Inventors: Tadashi Mochizuki; Shigeomi Sato; Takanori Akiyoshi; Akiko Sakashita; Yohichi Ishibashi, all of Tokyo, Japan

[73] Assignee: NKK Corporation, Japan

[21] Appl. No.: 722,276

[22] PCT Filed: Jun. 12, 1996

[86] PCT No.: PCT/JP96/01585

§ 371 Date: Oct. 9, 1996

§ 102(e) Date: Oct. 9, 1996

[87] PCT Pub. No.: WO96/42005

PCT Pub. Date: Dec. 27, 1996

[30] Foreign Application Priority Data

Jun. 12, 1995 [JP] Japan .................. 7-170239

[51] Int. Cl.[6] .................. G01N 1/00; G01N 21/63; G01N 21/72; G01N 21/73
[52] U.S. Cl. .................. 356/315; 356/36; 356/316; 356/318
[58] Field of Search .................. 356/237, 430–431, 356/315–318, 36; 250/359.39, 359.4, 359.44, 359.48

[56] References Cited

U.S. PATENT DOCUMENTS

| | | | |
|---|---|---|---|
| 3,602,595 | 8/1971 | Dahlquist et al. | 356/36 |
| 3,791,743 | 2/1974 | Cody et al. | 356/313 |
| 4,598,577 | 7/1986 | Jowitt et al. | 356/36 |
| 4,615,225 | 10/1986 | Sainz | 356/36 |
| 5,537,206 | 7/1996 | Akiyoshi et al. | 356/315 |

FOREIGN PATENT DOCUMENTS

| | | |
|---|---|---|
| 62-162947 | 7/1987 | Japan . |
| 3-118440 | 5/1991 | Japan . |
| 7-72047 | 3/1995 | Japan . |
| 7-128237 | 5/1995 | Japan . |

*Primary Examiner*—David C. Nelms
*Assistant Examiner*—Jason D. Vierra-Eisenberg
*Attorney, Agent, or Firm*—Akin, Gump, Strauss, Hauer & Feld, L.L.P.

[57] ABSTRACT

A method for detecting a cause of an abnormal portion present on a surface of a steel product, which comprises the steps of: condensing a pulsed laser beam, irradiating the pulsed laser beam thus condensed onto an abnormal portion present on a surface of a steel product and a vicinity thereof, limiting pulse energy density of the pulsed laser beam at an irradiation point of the pulsed laser beam on the surface of the steel product within a range of from 10 kW/mm$^2$ to 100 MW/mm$^2$; causing the irradiation point of the pulsed laser beam to zigzag-move throughout the entire region containing the abnormal portion and the vicinity thereof, to vaporize a surface portion of the steel product in the zigzag-moving region of the irradiation point, and converting the resultant vapor into fine particles, so as to collect samples of the abnormal portion and the vicinity thereof on the surface of the steel product in the form of fine particles; and continuously analyzing chemical compositions of the thus collected samples in the form of fine particles to detect a cause of an abnormal portion present on the surface of the steel product.

4 Claims, 4 Drawing Sheets

METHOD FOR DETECTING CAUSE OF ABNORMAL PORTION PRESENT ON SURFACE OF STEEL PRODUCT

FIELD OF THE INVENTION

The present invention relates to a method for rapidly and accurately detecting a cause of an abnormal portion present on a surface of a steel product.

BACKGROUND OF THE INVENTION

In addition to abnormal portions caused by flaws mechanically produced during a rolling process or the like, an abnormal portion may be produced on a surface of a steel product by means of a cause such as non-metallic inclusions in steel, powder added to molten steel in a mold during a continuous casting, brick chips entrapped into steel, or scales not separated. In order to prevent such an abnormal portion from being produced, it is necessary to rapidly and accurately detect a cause of such an abnormal portion and promptly eliminate the cause.

An abnormal portion on a surface of a steel product caused by non-metallic inclusions in steel is produced on the surface of the steel product in such a manner that non-metallic inclusions present in steel reach the surface of the steel product through a rolling, and are linearly rolled in the rolling direction. A cause of the abnormal portion can be clarified on the basis of an investigation of a difference in chemical composition between the abnormal portion and a normal portion in the vicinity of the abnormal portion.

More specifically, a chemical composition of an abnormal portion linearly elongated in the rolling direction, produced on the surface of the steel product, and a chemical composition of a normal portion in the vicinity of the abnormal portion are subjected to a linear analysis across these portions to compare the chemical composition of the abnormal portion with that of the normal portion in the vicinity of the abnormal portion. As a result, for example, when only such elements as Ca and Al which form non-metallic inclusions are detected with high concentrations in the abnormal portion, production of the abnormal portion can be estimated to be due to the presence of an $Al_2O_3 \cdot CaO$ composite non-metallic inclusion. In the case where no particular element is detected with a high concentration in the abnormal portion, in contrast, production of the abnormal portion can be estimated to be due to the non-separation of scales or the rolling, whereby it is possible to eliminate the cause of production of the abnormal portion by the separation of scales or by investigating the rolling process or the like.

The foregoing linear analysis has conventionally been carried out by means of an electron beam radiation fluorescent X-ray microanalysis (hereinafter referred to as the "XMA") or an electron microscopic observation. The linear analysis based on such conventional methods requires, however, pretreatments such as a cutting of a sample to incorporate same into an analyzing instrument and a surface preparation of the sample for observing same, thus leading to a problem of requiring a long period of time for obtaining a result of analysis. Since the electron microscopic observation is a micro-observation, a problem is that the observation is one-sided and it is inevitable to overlook non-metallic inclusions or the like (hereinafter referred to as the "origins") present outside the field of view of the electron microscope.

As a means to solve the problems as described above, a method known as the discharge emission spectrochemical analysis is proposed. For example, Japanese Patent Provisional Publication No. 62-162,947 published on Jul. 18, 1987 discloses a method for detecting a cause of an abnormal portion, which comprises the steps of:

causing electric discharge between an electrode and a surface of a steel sheet to continuously discharge-scan the surface of the steel sheet from a normal portion thereof toward an abnormal portion, and comparing intensity of an emission spectrum of the abnormal portion with intensity of an emission spectrum of the normal portion, both of which emission spectra have been obtained by means of the discharge-scanning (hereinafter referred to as the "prior art").

The discharge emission spectrochemical analysis of the prior art, involves the following problems: Electric discharge takes place between the scanning electrode and the surface of the steel sheet. Since the spectrochemical analysis based on the discharge emission is affected by electric conductivity of the surface of the steel sheet and/or a surface shape thereof, it is difficult to accurately detect chemical compositions at various portions of the surface of the steel sheet by the application of the prior art. While it is possible to excite elements on the surface of the steel sheet by electric discharge, it is impossible to excite elements present at a depth of about several tens of μm from the surface toward the interior of the steel sheet, thus making it impossible to accurately detect a cause of the abnormal portion by means of the prior art. Because of a large electric discharge area (i.e., a large arc diameter), the prior art has a poor positional resolution of the origins. It is therefore very difficult to detect the chemical composition and the cause of a narrow linear abnormal portion by means of the prior art.

An object of the present invention is therefore to provide a method which solves the conventional problems as described above, permits rapid and accurate detection of a cause of an abnormal portion present on a surface of a steel product without being affected by electric conductivity of the surface of the steel product and/or a surface shape thereof, makes it possible furthermore to detect chemical compositions of substances resulting in the cause of the abnormal portion, which substances are present at a large depth in the interior of the steel product, is excellent in a positional resolution of origins., and permits an accurate application of a linear analysis for detecting changes in a chemical composition of the origin in a certain direction.

SUMMARY OF THE INVENTION

In accordance with one of the features of the present invention, there is provided a method for detecting a cause of an abnormal portion present on a surface of a steel product, which comprises the steps of:

condensing a pulsed laser beam, irradiating said pulsed laser beam thus condensed onto an abnormal portion present on a surface of a steel product and a vicinity thereof, limiting pulse energy density of said pulsed laser beam at an irradiation point of said pulsed laser beam on the surface of said steel product within a range of from 10 $kW/mm^2$ to 100 $MW/mm^2$;

causing said irradiation point of said pulsed laser beam to zigzag-move throughout the entire region containing said abnormal portion and the vicinity thereof, to vaporize a surface portion of said steel product in said zigzag-moving region of said irradiation point, and converting the resultant vapor into fine particles, so as to collect samples of said abnormal portion and the vicinity thereof on the surface of said steel product in the form of fine particles; and continuously analyzing chemical compositions of the thus collected samples in the form of fine particles to detect a cause of an abnormal portion present on the surface of said steel product.

In accordance with another feature of the present invention, there is provided a method for detecting a cause of an abnormal portion present on a surface of a steel product, wherein:

said zigzag-moving region of said irradiation point of said pulsed laser beam comprises a rectangle having a shorter side corresponding to a width of at least 2 mm formed by amplitude of said zigzag movement of said irradiation point, on the one hand, and a longer side corresponding to an advancing distance of said zigzag movement of said irradiation point, on the other hand; and said samples are collected, in said zigzag-moving region of said irradiation point of said pulsed laser beam, at a depth within a range of from 20 to 200 μm from the surface of said steel product toward the interior thereof.

DETAILED DESCRIPTION OF PREFFERED EMBODIMENTS

Figure 1:
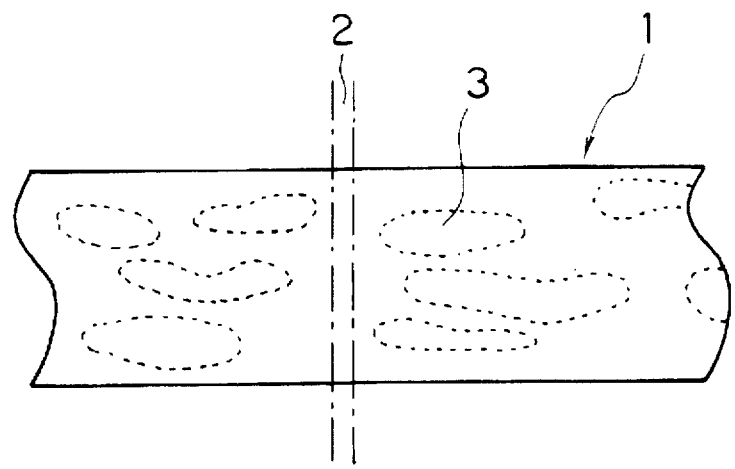
FIG. 1 is a descriptive view illustrating the relationship between a width of an irradiating region of a pulsed laser beam and positions of scattered origins in the case where the width of the irradiating region is small.

From the above-mentioned point of view, extensive studies were carried out to develop a method which permits rapid and accurate detection of a cause of an abnormal portion present on a surface of a steel product without being affected by electric conductivity of the surface of the steel product and/or a surface shape thereof, makes it possible furthermore to detect chemical compositions of substances resulting in the cause of the abnormal portion, which substances are present at a large depth in the interior of the steel product, is excellent in a positional resolution of origins, and permits an accurate application of a linear analysis for detecting changes in a chemical composition in a certain direction.

As a result, the following findings were obtained: When condensing a pulsed laser beam and irradiating the pulsed laser beam thus condensed onto an abnormal portion present on a surface of a steel product and a vicinity thereof, samples can be effectively collected from the abnormal portion and the vicinity thereof by limiting pulse energy density of the pulsed laser beam at an irradiation point of the pulsed laser beam on the surface of the steel product within a range of from 10 kW/mm$^2$ to 100 MW/mm$^2$, and it is possible to detect a cause of the abnormal portion present on the surface of the steel product by continuously analyzing a chemical composition of the samples thus collected. In addition, a more effective collection of samples can be accomplished by collecting samples from a region (i.e., an irradiating region of the pulsed laser beam) having a width of at least 2 mm, and at a depth within a range of from 20 to 200 μm from the surface of the steel product toward the interior thereof.

The present invention was made on the basis of the foregoing findings. The method of the present invention will now be described in detail below.

When condensing a pulsed laser beam by means of an optical instrument, and irradiating the pulsed laser beam thus condensed onto a surface of a steel product, since pulse energy density at an irradiation point of the pulsed laser beam is very large, the surface portion of the steel product at the irradiation point is heated to a high temperature and is vaporized. The thus vaporized surface portion of the steel product is immediately solidified into fine particles. This phenomenon is not limited to a steel product, but occurs similarly in case of a substance having a high boiling point such as ceramics. Even when electrically non-conductive origins are present at a high density in the surface portion of the steel product, therefore, it is possible to charge energy therein by means of a pulsed laser beam. Samples can therefore be collected without fail from the surface portion of the steel product to be detected irrespective of its electric conductivity. The irradiation point of the pulsed laser beam, being determined by the direction of the beam, is never affected by the surface shape of the steel product, unlike the electric discharge point.

When estimating a cause of an abnormal portion on the surface of the steel product, a concentration of components is used as a ground. The components used as grounds include Na, Ca, Al, Mg and Si, which are often present in the form of compounds such as an oxide, a nitride or a carbide. In order to decompose or vaporize these compounds having a high boiling point, therefore, pulse energy density of the pulsed laser beam at the irradiation point must be at least 10 kW/mm$^2$.

The amount of vapor of the components of the steel product increases according as pulse energy density of the pulsed laser beam at the irradiation point becomes larger. With a pulse energy density of over 100 MW/mm$^2$, however, a breakdown phenomenon occurs in which an atmosphere is ionized to produce plasma before the pulsed laser beam reaches the surface of the steel product. Upon occurrence of such a breakdown phenomenon, pulse energy of the pulsed laser beam is consumed by the atmosphere, and is not charged into the steel product. It becomes therefore impossible to collect samples from the surface portion of the steel product. Pulse energy density of the pulsed laser beam at the irradiation point thereof should therefore be limited to up to 100 MW/mm$^2$.

In the present invention, for the reason as described above, upon condensing a pulsed laser beam and irradiating the thus condensed pulsed laser beam onto an abnormal portion present on a surface of a steel product and a vicinity thereof, it is important to limit pulse energy density at the irradiation point of the pulsed laser beam within a range of from 10 kW/mm$^2$ to 100 MW/mm$^2$.

When moving the irradiation point of the condensed pulsed laser beam irradiated onto the surface of the steel product with a pulse energy density within the foregoing range to cause the irradiation point to pass through a boundary between the normal portion and the abnormal portion on the surface of the steel product, vapor produced from the surface portion of the steel product shows the following changes at a passing point on the boundary. After vaporization of the components of the normal portion, components of the abnormal portion is vaporized. Or, after vaporization of the components of the normal portion, the components of the abnormal portion is vaporized, and then the components of the normal portion is vaporized again. The resultant vapor is immediately solidified into fine particles as described above. Therefore, by collecting samples in the form of fine particles from the normal portion and the abnormal portion, transferring the thus obtained samples to a measuring instrument, and continuously analyzing chemical compositions thereof, there is available concentration of the components corresponding to positions of the irradiation point of the pulsed laser beam. Consequently, a component which shows a sharp change in concentration in the abnormal portion, if any, demonstrates that this component has a close relationship with the cause of the abnormal portion.

Figure 2:
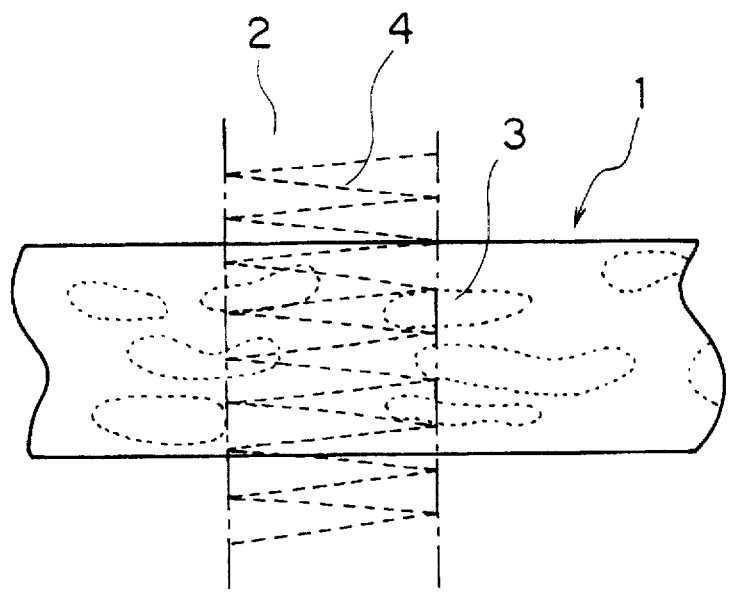
FIG. 2 is a descriptive view illustrating the relationship between a width of an irradiating region of a pulsed laser beam and positions of scattered origins in the case where the width of the irradiating region is large.

FIGS. 1 and 2 illustrate the relationship between a width of a zigzag-moving region (i.e., an irradiating region) of an irradiation point of a pulsed laser beam and positions of scattered origins. FIG. 1 covers a case with a small width of the irradiating region in which the width of the irradiating region is, for example, equal to a beam diameter of the pulsed laser beam. In FIG. 1, 1 is a test piece of a steel product, 2 is a width of the irradiating region, and 3 represents scattered origins. FIG. 2 covers a case with a large width of the irradiating region. In FIG. 2, 1 is a test piece of a steel product, 2 is a width of the irradiating region, 3 represents scattered origins, and 4 shows a schematic locus of a zigzag movement of the irradiation point of a pulsed laser beam. Actually, the irradiation point of the pulsed laser beam zigzag-moves in such a manner that a zigzag line covers a region to be scanned for detection leaving no gap. As a result, the zigzag-moving region (i.e., the irradiating region) of the irradiation point comprises a rectangle having a shorter side corresponding to a width of at least 2 mm formed by amplitude of the zigzag movement of the irradiation point, on the one hand, and a longer side corresponding to a advancing distance of the zigzag movement of the irradiation point, on the other hand.

The origins in the steel product are not necessarily present uniformly throughout the entire abnormal portion, but may be ununiformly scattered. When a line width in a linear analysis (i.e., the width of the irradiating region) is small, therefore, scattered origins may be overlooked, thus leading to an erroneous estimation of a cause of the abnormal portion. Particularly, when a thin linear abnormal portion is present, probability of overlooking thereof is rather high.

In order to accurately detect the thin linear abnormal portion as described above without overlooking thereof, it suffices to widen the line width of the linear analysis (i.e., the width of the irradiating region). As described above, when the width 2 of the irradiating region on the test piece 1 is small as shown in FIG. 1, it may happen that the irradiation point does not pass on the origins 3. In such a case, it is therefore impossible to collect samples of the components of the origins 3 causing the abnormal portion.

When the width 2 of the irradiating region on the test piece 1 is large as shown in FIG. 2, in contrast, the irradiation point passes on the origins 3 without fail, thus making it possible to certainly collect samples of the components of the origins 3 causing the abnormal portion. Results of many tests carried out by the present inventors suggest that collection of samples of the components of the origins 3 is ensured by using a width 2 of at least 2 mm of the irradiating region. It is therefore preferable to select a width 2 of the irradiating region of at least 2 mm. With a width of the irradiating region of over 10 mm, on the other hand, the collection time of samples becoming longer poses problems in analyzing efficiency. The width of the irradiating region should therefore be limited preferably to up to 10 mm.

In order to increase the width of the irradiating region, it is not always necessary to increase the diameter of the irradiation point, i.e., the beam diameter of the pulsed laser beam. Even with a small beam diameter of the pulsed laser beam, it is possible to increase the width of the irradiating region by moving the irradiation point of the pulsed laser beam along the zigzag locus 4 as shown in FIG. 2. In this case, a smaller angle formed at a turn of the zigzag locus 4 leads to a higher positional resolution of origins, thus making it possible to detect sparsely scattered origins.

What should be noted about the state of presence of origins in the steel product is that, when the origins are non-metallic inclusions, linear abnormal portions which have not reached the surface of the steel product may exist in the interior thereof. More specifically, non-metallic inclusions exist at a relatively small depth from the surface of a steel sheet toward the interior thereof in the case of the steel sheet having been rolled with a very small thickness, whereas, non-metallic inclusions tend to be distributed within a depth range of from 20 to 200 μm from the surface of a steel sheet toward the interior thereof in the case of the steel sheet having been rolled with a relatively large thickness.

When irradiating a pulsed laser beam with a pulse energy density within the scope of the present invention onto a surface of a steel sheet containing a linear abnormal portion extending in the rolling direction to collect samples, and detecting a component causing the abnormal portion on the basis of concentration of the component in the samples, the effect of a sampling depth on a detection accuracy will be described below with reference to FIGS. 3 to 6.

An irradiating region was set so as to cause the irradiation point of the pulsed laser beam to move across the linear abnormal portion extending in the rolling direction on the surface of the steel sheet. More specifically, the irradiating region was set so that the width direction of the irradiating region was in parallel with the linear abnormal portion, and the linear abnormal portion was located at the center of the longitudinal direction of the irradiating region. The irradiation point was caused to zigzag-move with a width of the irradiating region of 2 mm to collect samples. Then, on the basis of the samples thus collected, a detection intensity ratio (which corresponds to an emission spectrum intensity ratio as calculated with an intensity of an emission spectrum of elemental iron as the denominator, and with an intensity of an emission spectrum of an element in the sample as the numerator) was determined, and a component causing the abnormal portion was detected by means of a detection intensity curve expressing the detection intensity ratio thus determined.

FIGS. 3 to 6 are graphs illustrating typical detection intensity curves in cases where samples of a surface portion of a steel produt are collected at several depths from the surface of the steel product toward the interior thereof. In FIGS. 3 to 6, the abscissa represents a line length (i.e., an advancing distance of the zigzag movement of the irradiation point in the longitudinal direction of the irradiating region), and the ordinate, the detection intensity ratio.

Figure 3:
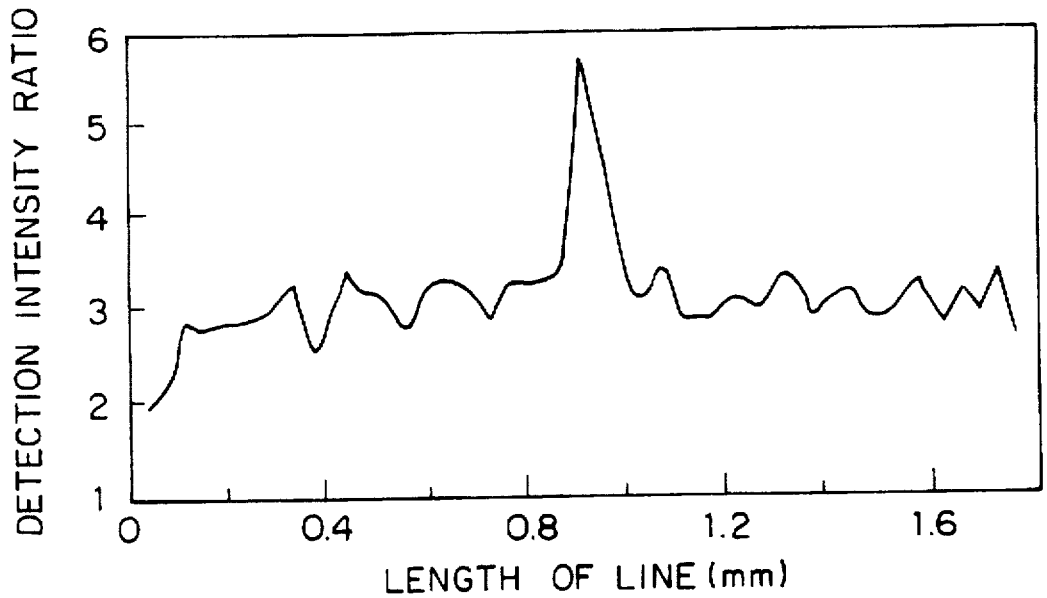
FIG. 3 is a graph illustrating a typical detection intensity curve in the case where samples of a surface portion of a steel product are collected at a depth of 30 μm from the surface of the steel product toward the interior thereof.
Figure 4:
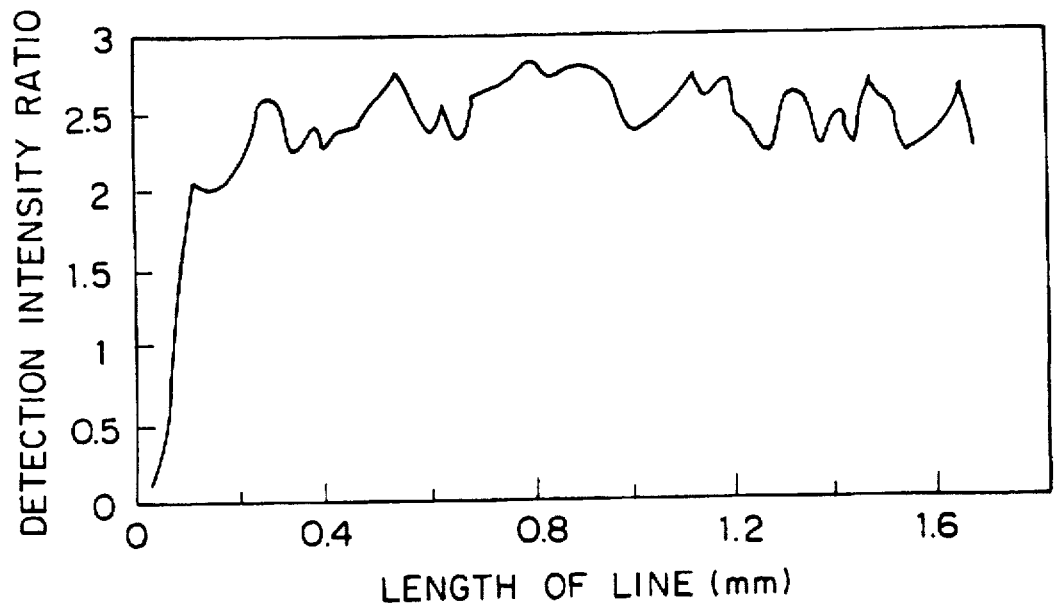
FIG. 4 is a graph illustrating a typical detection intensity curve in the case where samples of a surface portion of a steel product are collected at a depth of 10 μm from the surface of the steel product toward the interior thereof.

FIG. 3 is a graph illustrating a typical detection intensity curve in the case where samples of a surface portion of a steel product are collected at a depth of 30 µm from the surface of the steel product toward the interior thereof. As shown in FIG. 3, with a sampling depth of 30 µm from the surface of the steel product toward the interior thereof, there appears a large detection intensity ratio near a line length (i.e., an advancing distance of the zigzag movement of the irradiation point in the longitudinal direction of the irradiating region) of 0.9 mm, suggesting a remarkable change in concentration of a component. More specifically, the detection intensity curve suggests that intensity of an emission spectrum intensity of an element in the sample near a line length of 0.9 mm is about six times as large as that of iron. FIG. 4 is a graph illustrating a typical detection intensity curve in the case where samples of a surface portion of a steel product are collected at a depth of 10 µm from the surface of the steel product toward the interior thereof. As shown in FIG. 4, with a sampling depth of 10 µm from the surface of the steel product toward the interior thereof, a remarkable change in detection intensity ratio as observed in FIG. 3 does not appear, and therefore, a component causing the abnormal portion cannot be detected. As is clear from the foregoing, a detection hit ratio of a linear abnormal portion is low when collecting the samples at a depth of under 20 µm from the surface of the steel product toward the interior thereof.

Figure 5:
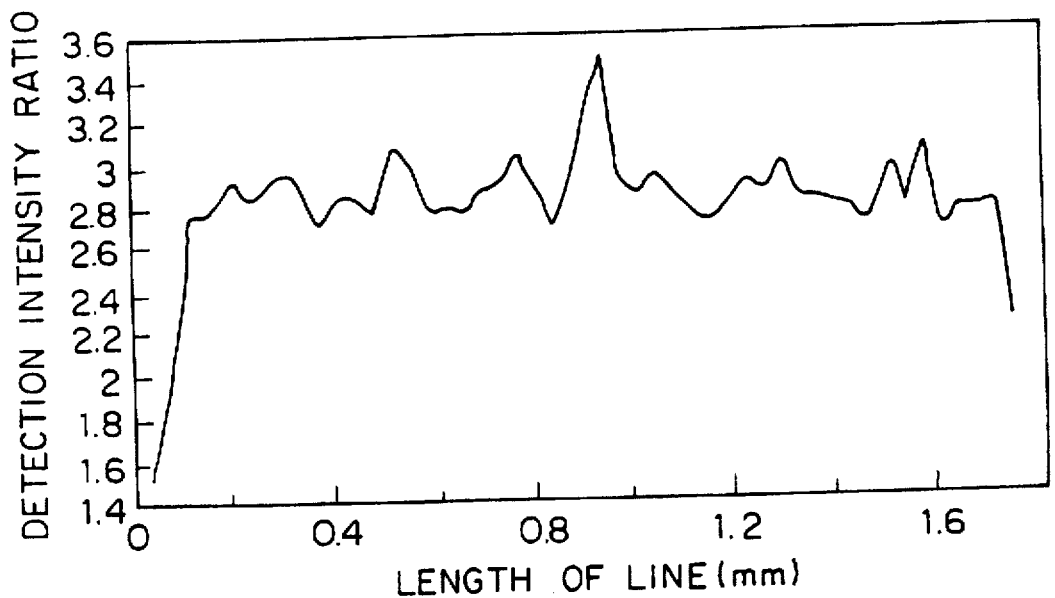
FIG. 5 is a graph illustrating a typical detection intensity curve in the case where samples of a surface portion of a steel product are collected at a depth of 150 μm from the surface of the steel product toward the interior thereof.
Figure 6:
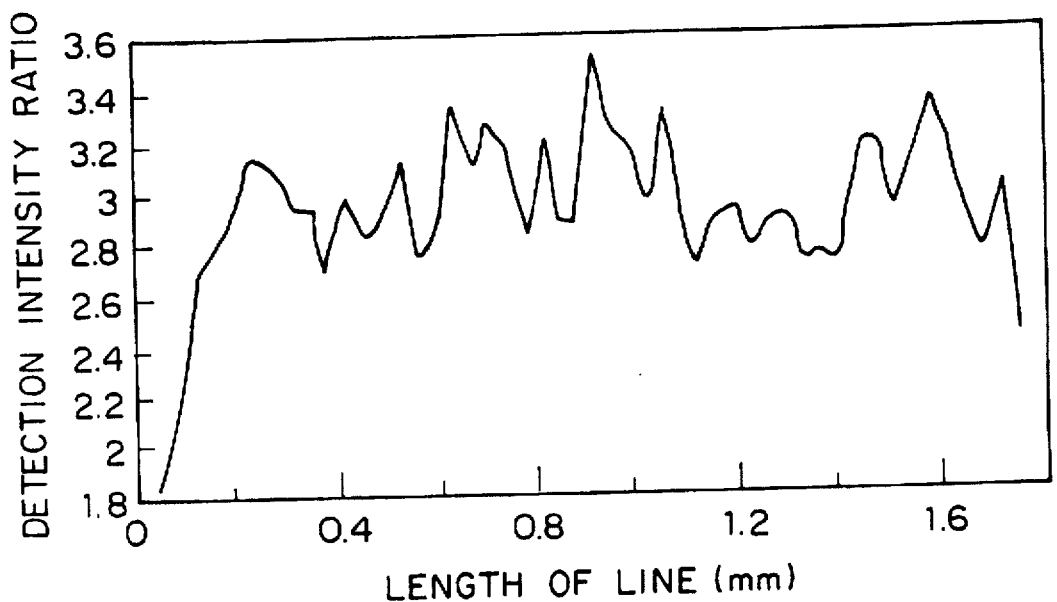
FIG. 6 is a graph illustrating a typical detection intensity curve in the case where samples of a surface portion of a steel product are collected at a depth of 230 μm from the surface of the steel product toward the interior thereof.

When collecting samples at a depth of over 200 µm from the surface of the steel product toward the interior thereof, in contrast, the amount of collected samples is excessively large, leading to a lower concentration of a component causing the abnormal portion, hence to a lower detection sensitivity. FIG. 5 is a graph illustrating a typical detection intensity curve in the case where samples of a surface portion of a steel product are collected at a depth of 150 µm from the surface of the steel product toward the interior thereof, and FIG. 6 is a graph illustrating a typical detection intensity curve in the case where samples of a surface portion of a steel product are collected at a depth of 230 µm from the surface of the steel product toward the interior thereof. With a sampling depth of 150 µm from the surface of the steel product toward the interior thereof, as shown in FIG. 5, there appears a large detection intensity ratio near a line length (i.e., an advancing distance of the zigzag movement of the irradiation point in the longitudinal direction of the irradiating region) of 0.9 mm, suggesting a remarkable change in concentration of a component. In contrast, with a sampling depth of 230 µm from the surface of the steel product toward the interior thereof, as shown in FIG. 6, remarkability of the change in concentration of the component is lower than that shown in FIG. 5.

In the case of a steel sheet having a very small thickness, the irradiated pulsed laser beam penetrates the steel sheet, and reaches another member located below the steel sheet, and the another member may be detected. When irradiating a pulsed laser beam, therefore, it is necessary to take account of an irradiating depth thereof. In general, it suffices to select an irradiating depth of the pulsed laser beam of a half of a thickness of the steel product to be measured. In the case of a pulsed laser beam, it is possible to easily control the irradiating depth, i.e., the sampling depth.

The irradiating depth of a pulsed laser beam is controlled as follows: An amount of the steel product vaporized by the pulsed laser beam depends upon an amount of energy of the pulsed laser beam charged into the steel product. An irradiating depth of the pulsed laser beam depends upon an amount of energy of the pulsed laser beam charged into a unit area. The amount of energy of the pulsed laser beam charged into the steel product is the product of an average output and an irradiation time of the pulsed laser beam. An area of the irradiating region of the pulsed laser beam, i.e., an irradiation area, is the product of the line width (i.e., the width of amplitude of the zigzag movement of the irradiation point in the width direction of the irradiating region) and the line length (i.e., the advancing distance of the zigzag movement of the irradiation point in the longitudinal direction of the irradiating region).

The irradiating depth of the pulsed laser beam is therefore determined from a value obtained by dividing the product of the average output and the irradiation time of the pulsed laser beam (i.e., the amount of energy of the charged pulsed laser beam) by the product of the line width and the line length (i.e., the irradiation area). Since the line length is the product of a line speed (i.e., a speed of advance of the zigzag movement of the irradiation point in the longitudinal direction of the irradiating region) and the irradiation time, the irradiating depth of the pulsed laser beam is determined from a value obtained by dividing the average output of the pulsed laser beam by the product of the line width and the line speed in accordance with the following formula(1):

(irradiating depth) ∝ (average output × (1)

irradiation time)/(line width × line length) =

(average output)/(line width × line speed)

That is, with a constant average output of the pulsed laser beam, a higher line speed leads to a smaller sampling depth, and a lower line speed leads to a larger sampling depth. With a constant line speed, on the other hand, a larger average output leads to a larger sampling depth. With the optimum irradiating depth and line speed, furthermore, the positional resolution of origins can be improved by increasing the average output and widening the line width.

Movement of the irradiation point of the pulsed laser beam can be controlled through an optical operation while keeping a pulsed laser oscillator in the fixed state. More specifically, the irradiation point of the pulsed laser beam can be moved through rotation of a reflector, parallel movement of a condensing lens which condenses the pulsed laser beam, or a combination thereof.

EXAMPLES

Now, the present invention will be described further in detail by means of examples. For a plurality of abnormal portions present on a surface of a steel sheet, samples were collected and analyzed by the method of the present invention to evaluate the result of analysis. For analyzing and evaluating purposes, test pieces of a steel sheet each having a thickness within a range of from 0.2 to 2 mm were used.

A Q-switched YAG laser (YAG being abbreviation of yttrium aluminum garnet) was employed as a pulsed laser oscillator. A pulsed laser beam emitted from the pulsed laser oscillator (not shown), was turned by a reflector toward a surface of the test piece. The pulsed laser beam was then condensed by means of a condensing lens, and the pulsed laser beam thus condensed was irradiated onto the surface of the test piece. Advance of an irradiation point of the pulsed laser beam in the longitudinal direction of an irradiating region was accomplished by moving the condensing lens in the advancing direction of the irradiation point. When causing the irradiation point to zigzag-move, the reflector was zigzag-moved so that the angle of the reflector changed relative to the width direction of the irradiating region. The width of the irradiating region was determined on the basis of the maximum value of changes in the angle of the reflector as described above.

Collection of samples from the surface of the test piece, i.e., from the surface of the steel sheet by means of the irradiation of the pulsed laser beam was accomplished by the used of a fine particles collecting cell (not shown). More specifically, the surface of the steel sheet was airtightly covered with an opening of the fine particles collecting cell through a sealing member, and an argon gas was introduced through an inert gas inlet port into the fine particles collecting cell to keep an inert atmosphere in the interior of the fine particles collecting cell. A ceiling of the fine particles collecting cell was made of quartz glass, and the pulsed laser beam thus condensed permeated the ceiling made of quartz glass to form an irradiation point on the surface of the steel sheet. Samples of the surface portion of the steel sheet, vaporized by the pulsed laser beam and converted into fine particles, was introduced by the argon gas from the fine particles collecting cell into a component measuring instrument, in which components of the fine particles were analyzed.

An inductively coupled plasma atomic emission spectrometer (hereinafter referred to as the "IPC spectrometer") was used as the component measuring instrument. When presence of components causing the abnormal portion is anticipated, an atomic absorption spectrometer may be used, not limiting to the IPC spectrometer as described above, and when the amount of components causing the abnormal portion is small, a mass analyzing instrument may be used as well.

A pulsed laser beam was irradiated onto the surface of each test piece of the steel sheet under the pulsed laser beam irradiating conditions and the sampling conditions shown in Table 1, and samples in the form of fine particles were collected for analysis, and the analysis results were evaluated.

Table 1 shows the pulsed laser beam irradiating conditions, the sampling conditions and evaluation of the analysis results for samples collected according to a method within the scope of the present invention (hereinafter referred to as the "Samples of the Invention") Nos. 1 to 11, samples collected according to a method outside the scope of the present invention, (hereinafter referred to as the "Samples for Comparison") Nos. 1 and 2, and a sample collected according to a conventional method outside the scope of the present invention (i.e., the discharge emission spectrochemical analysis) (hereinafter referred to as the "Sample for Comparison) No. 3.

TABLE 1

| | Pulsed laser beam irradiating conditions | | | | | Sampling conditions | | | |
| --- | --- | --- | --- | --- | --- | --- | --- | --- | --- |
| No. | Average output (W) | Frequency (Hz) | Pulse half width (S) | Beam diameter (mm) | Pulse energy density (W/mm$^2$) | Line speed (mm/min) | Width (mm) | Depth (μm) | Evaluation |
| Sample of the Invention | | | | | | | | | |
| 1 | 5 | 10 | $2.5 \times 10^{-4}$ | 0.45 | $1.26 \times 10^4$ | 2 | 2 | 75 | ⊚ |
| 2 | 2 | 10 | $5.0 \times 10^{-8}$ | 0.20 | $5.70 \times 10^7$ | 2 | 2 | 30 | ⊚ |
| 3 | 5 | 1000 | $1.0 \times 10^{-7}$ | 0.20 | $3.18 \times 10^6$ | 3 | 6 | 20 | ⊚ |
| 4 | 5 | 50000 | $1.5 \times 10^{-8}$ | 0.05 | $3.40 \times 10^6$ | 2 | 2 | 75 | ⊚ |
| 5 | 10 | 1000 | $1.0 \times 10^{-7}$ | 0.25 | $2.04 \times 10^6$ | 12 | 2 | 25 | ⊚ |
| 6 | 10 | 1000 | $1.0 \times 10^{-7}$ | 0.25 | $2.04 \times 10^6$ | 1.5 | 2 | 200 | ⊚ |
| 7 | 40 | 2000 | $1.0 \times 10^{-7}$ | 0.45 | $1.26 \times 10^6$ | 12 | 3 | 67 | ⊚ |
| 8 | 5 | 5000 | $1.5 \times 10^{-8}$ | 0.25 | $1.36 \times 10^6$ | 6 | 1 | 50 | ○ |
| 9 | 10 | 1000 | $1.0 \times 10^{-7}$ | 0.25 | $2.04 \times 10^6$ | 12 | 3 | 17 | ○ |
| 10 | 12 | 1000 | $1.0 \times 10^{-7}$ | 0.25 | $2.04 \times 10^6$ | 1.5 | 2 | 240 | ○ |
| 11 | 3 | 5000 | $1.5 \times 10^{-8}$ | 0.20 | $1.27 \times 10^6$ | 3 | 1 | 15 | □ |
| Samples for Comparison | | | | | | | | | |
| 1 | 3 | 10 | $2.5 \times 10^{-4}$ | 0.45 | $7.55 \times 10^3$ | 2 | — | — | x |
| 2 | 2 | 10 | $2.0 \times 10^{-8}$ | 0.30 | $1.40 \times 10^8$ | 2 | — | — | x |
| 3 | Discharging conditions of conventional method: Voltage: 400 V Discharge frequency: 800 Hz Discharge point: 6 mmφ | | | | | 30 | 6 | — | x |

Evaluation of the analysis results comprised, for an abnormal portion of which components causing the abnormal portion had previously been confirmed by means of the conventional electron beam radiation fluorescent X-ray microanalysis (hereinafter referred to as the "XMA"), conducting a linear analysis under the conditions shown in Table 1, and assessing the analysis result by means of a detection hit ratio as prescribed below.

Detection hit ratio:

(Number of samples of which a component causing an abnormal portion has been confirmed by the method shown in Table 1)/(Number of samples of which a component causing an abnormal portion has been confirmed by the conventional XMA)

In Table 1, the evaluation results of the detection hit ratio are expressed by the following symbols:

◎ : An average detection hit ratio of at least 90%;

○ : An average detection hit ratio of from 80% to under 90%;

□ : An average detection hit ratio of from 70% to under 80%;

× : An average detection hit ratio of under 70%.

As is clear from Table 1, a detection hit ratio of at least 70% was obtained in all of the Samples of the Invention Nos. 1 to 11. Particularly, in the Samples of the Invention Nos. 1 to 7 in which the line width (i.e., the width of the irradiating region) was at least 2 mm and the sampling depth was within a range of from 20 to 200 µm, a detection hit ratio of at least 90% was obtained. In the Sample of the Invention No. 8 in which the line width was under 2 mm, the Sample of the invention No. 9 in which the sampling depth was smaller than 20 µm, and the Sample of the Invention No. 10 in which the sampling depth was over 200 µm, the detection hit ratio was within a range of from 70 to 80%. In the Sample of the Invention No. 11 in which the line width was under 2 mm and the sampling depth was smaller than 20 µm, the detection hit ratio was 70s of %. The reason was that non-metallic inclusions located at a large depth in the steel sheet could not be detected.

In the Sample for Comparison No. 1 in which pulse energy density was small outside the scope of the present invention, in contrast, it was almost impossible to vaporize the surface portion of the steel sheet to collect samples. In the Sample for Comparison No. 2 in which pulse energy density was large outside the scope of the present invention, the breakdown phenomenon occurred, thus making it impossible to vaporize the surface portion of the steel sheet to collect samples as well. As a result, in the Samples for Comparison Nos. 1 and 2, a component causing an abnormal portion could not be detected. In the Sample for Comparison No. 3 based on the conventional method, it was impossible to detect thin abnormal portions present on the surface of the steel sheet and non-metallic inclusions existing at a large depth in the interior of the steel product, resulting in a detection hit ratio of under 70%.

Figure 7:
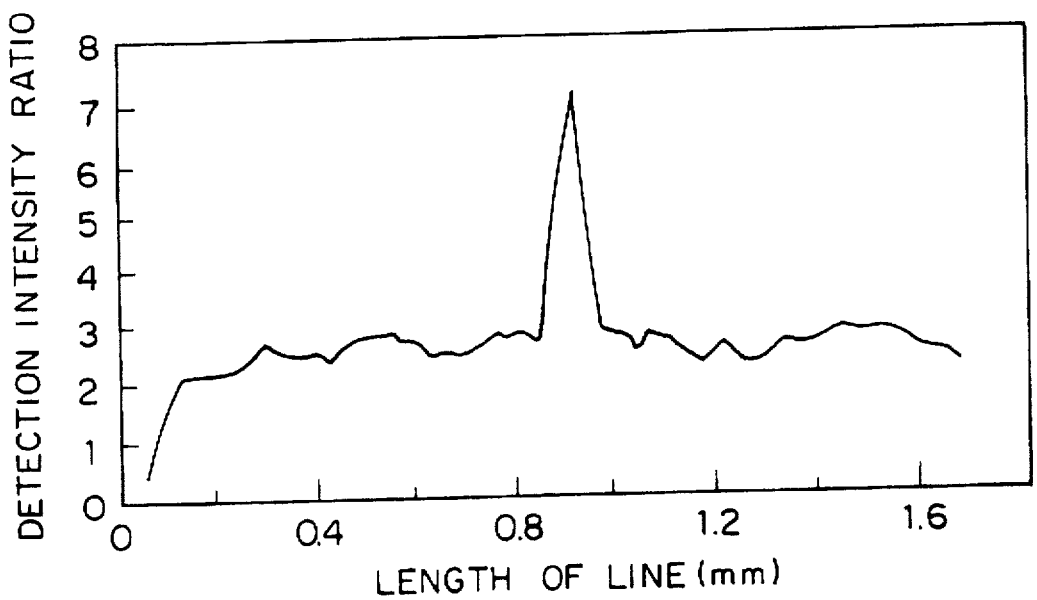
FIG. 7 is a graph illustrating a detecting intensity curve of Al in the Sample of the Invention No. 3 according to the method of the present invention.
Figure 8:
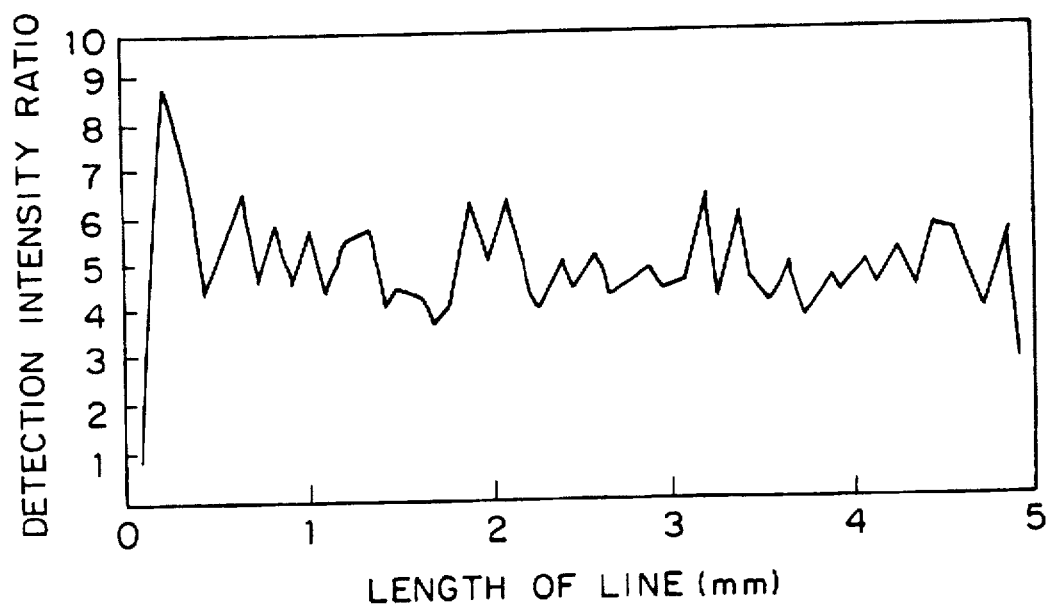
FIG. 8 is a graph illustrating a detecting intensity curve of Al in the Sample for Comparison No. 3 according to a conventional method outside the scope of the present invention.

FIG. 7 illustrates a detecting intensity curve of Al in the Sample of the Invention No. 3, and FIG. 8 illustrates a detecting intensity curve of Al in the Sample for Comparison No. 3 according to the conventional method outside the scope of the present invention. As is evident from a comparison between FIGS. 7 and 8, in the Sample of the Invention No. 3 shown in FIG. 7, a peak which exhibits a remarkably large detecting intensity of Al is observed near a line length of 0.9 mm, whereas, in the Sample for Comparison No. 3 shown in FIG. 8 according to the conventional method outside the scope of the present invention, no peak is observed which peak should appear near a line length of 2 to 3 mm, this line length corresponding to the vicinity of the line length of 0.9 mm in FIG. 7, and Al is not detected consequently.

In the linear analysis in the present invention, it takes a less period of time within a range of from several to several tens of minutes for a run of measurement, so that the linear analysis in the present invention can be evaluated as a rapid analysis.

EFFECT OF THE INVENTION

According to the present invention, as described above in detail, it is possible to rapidly and accurately detect a cause of an abnormal portion present on a surface of a steel product without being affected by electric conductivity of the surface of the steel product and/or a surface shape thereof, to detect substances resulting in a cause of the abnormal portion, i.e., the origins, present at a large depth in the interior of the steel product, is excellent in a positional resolution of origins, and permits avoidance of overlooking non-metallic inclusions hidden in the interior of the steel product or origins scattered in a thin abnormal portion on the surface of the steel product, thus providing many industrially useful effects.

What is claimed is:

1. A method for detecting a cause of an abnormal portion present on a surface of a steel product, which comprises the steps of:

condensing a pulsed laser beam, irradiating said pulsed laser beam thus condensed onto an abnormal portion present on a surface of a steel product and a vicinity thereof to a specific depth, limiting pulse energy density of said pulsed laser beam at an irradiation point of said pulsed laser beam on the surface of said steel product within a range of from 10 kW/mm$^2$ to 100 MW/mm$^2$;

controlling said specific depth of said pulsed laser beam by a following formula:

(irradiating depth)∝(average output×irradiation time)/ (line width×line length)=(average output)/(line width×line speed);

causing said irradiation point of said pulsed laser beam to zigzag-move throughout the entire region containing said abnormal portion and the vicinity thereof, to vaporize a surface portion of said steel product in said zigzag-moving region of said irradiation point, and converting the resultant vapor into fine particles, so as to collect samples of said abnormal portion and the vicinity thereof on the surface of said steel product in the form of fine particles; and continuously analyzing chemical compositions of the thus collected samples in the form of fine particles to detect a cause of an abnormal portion present on the surface of said steel product.

2. A method as claimed in claim 1, wherein:

said zigzag-moving region of said irradiation point of said pulsed laser beam comprises a rectangle having a shorter side corresponding to a width of at least 2 mm formed by amplitude of said zigzag movement of said irradiation point, on the one hand, and a longer side corresponding to an advancing distance of said zigzag movement of said irradiation point, on the other hand.

3. A method as claimed in claim 1 or 2, wherein:

said samples are collected, in said zigzag-moving region of said irradiation point of said pulsed laser beam, at a depth within a range of from 20 to 200 µm from the surface of said steel product toward the interior thereof.

4. A method as claimed in claim 1, wherein:

said continuous analysis of the chemical composition of said samples is performed by comparing intensity of an emission spectrum of each of said samples with intensity of an emission spectrum of an element, which serves as a predetermined criterion.

\* \* \* \* \*